United States Patent
Beshore et al.

(10) Patent No.: US 12,310,945 B2
(45) Date of Patent: May 27, 2025

(54) CYCLOHEXYLGLYCINE DERIVATIVES AS SELECTIVE CYTOTOXIC AGENTS

(71) Applicant: Merck Sharp & Dohme LLC, Rahway, NJ (US)

(72) Inventors: Douglas C. Beshore, Lower Gwynedd, PA (US); Keith P. Moore, Doylestown, PA (US); Rajan Anand, Orinda, CA (US); Remond Moningka, Jersey City, NJ (US); William D. Shipe, Chalfont, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 182 days.

(21) Appl. No.: 18/145,127

(22) Filed: Dec. 22, 2022

(65) Prior Publication Data
US 2024/0252466 A1    Aug. 1, 2024

(51) Int. Cl.
*A61K 31/4035* (2006.01)
*A61K 45/06* (2006.01)
*A61P 31/18* (2006.01)

(52) U.S. Cl.
CPC .......... *A61K 31/4035* (2013.01); *A61K 45/06* (2013.01); *A61P 31/18* (2018.01)

(58) Field of Classification Search
CPC ...... A61K 31/4035; A61K 45/06; A61P 31/18
See application file for complete search history.

(56) References Cited

FOREIGN PATENT DOCUMENTS

| WO | WO-2007123686 A2 | * | 11/2007 | ............. | A61K 31/69 |
| WO | WO-2007127204 A2 | * | 11/2007 | ............. | A61K 31/00 |
| WO | WO-2014113750 A1 | * | 7/2014  | ............. | A61K 31/40 |

OTHER PUBLICATIONS

Meanwell, Nicholas A. "The Influence of Bioisosteres in Drug Design: Tactical Applications to Address Developability Problems." Topics in Medicinal Chemistry, 2013, pp. 283-381, doi: 10.1007/7355_2013_29. (Year: 2013).*
Meanwell, N.A., The Influence of Bioisosteres in Drug Design: Tactical Applications to Address Developability Problems, Topics in Medicinal Chemistry, vol. 9, p. 283-381, 2013.

* cited by examiner

*Primary Examiner* — Kortney L. Klinkel
*Assistant Examiner* — Donna M Nestor
(74) *Attorney, Agent, or Firm* — Patricia A. Shatynski; John C. Todaro

(57) ABSTRACT

The present disclosure is directed to cyclohexylglycine derivatives of Formula I

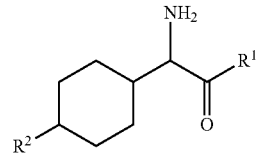

and their use as HIV-infected cell kill agents which accelerate the death of HIV GAG-POL expressing cells without concomitant cytotoxicity to HIV naïve cells.

10 Claims, No Drawings

CYCLOHEXYLGLYCINE DERIVATIVES AS SELECTIVE CYTOTOXIC AGENTS

BACKGROUND OF THE INVENTION

Human immunodeficiency virus (HIV) is the causative agent of acquired immunodeficiency syndrome (AIDS). In the absence of viral suppression, people living with HIV exhibit severe immunodeficiency which makes them highly susceptible to debilitating and ultimately fatal opportunistic infections. Multiple clinically approved antiretroviral drugs are available which demonstrate multi-log reductions in viral loads. Treated patients are at risk for acquiring mutations which render the virus in their bodies resistant to available therapies and rapid rebound of viremia is seen when therapy is removed, indicating that current regimens are not curative.

HIV is a retrovirus whose life cycle involves reverse transcription of a viral RNA genome into DNA via the enzyme reverse transcriptase and subsequent integration of the DNA copy into the host chromosomal DNA via the virally encoded integrase. Viral RNA is transcribed and viral proteins are translated using the host cellular machinery in conjunction with viral accessory proteins. Many viral proteins are contained within the GAG and GAG-POL polyproteins, with GAG containing structural proteins and GAG-POL, resulting from a frameshift near the carboxy-terminus of GAG, containing HIV protease (PR), reverse transcriptase (RT), and integrase (IN) viral enzymes, in addition to the structural proteins. GAG and GAG-POL are cleaved into individual proteins through the process of maturation, which occurs during budding of virions from the infected cell. At this time, GAG-POL dimerizes and the now dimeric HIV protease within the GAG-POL dimer forms an active enzyme that can cleave itself from the polyprotein and catalyze further cleavage to form the remaining viral enzymes and structural proteins.

Available antiretroviral drugs act by blocking the virus at different stages in the viral life cycle. For example, reverse transcriptase inhibitors target the viral reverse transcriptase and prevent the RNA genome from being copied into DNA, integrase inhibitors block the ability of the copied DNA from being integrated into the host cell, and PR inhibitors prevent viral maturation so that virions produced from cells treated with PR inhibitors are immature and non-infectious. Once integration has occurred, a cell is infected until it dies through either normal cell death pathways, accelerated death due to viral factors, or is targeted by the immune system. While most infected cells are expected to die within ~2 days of being infected, the rapid rebound of viremia when therapy is removed is an indication that infected cells remain, even after years on therapy (See, e.g., J. B. Dinoso et al., Proc. Natl. Acad. Sci. U.S.A., 2009, 106(23): 9403-9408). These latently infected and/or persistently virus-expressing cells that remain even during antiretroviral therapy are collectively termed the HIV reservoir and are the reason that people living with HIV require life-long treatment with a high level of adherence to maintain virus at undetectable levels.

The present disclosure is directed to cyclohexylglycine derivative compounds and their use for accelerating the death of HIV GAG-POL expressing cells without concomitant cytotoxicity to HIV naïve cells. In the absence of compounds such as those from the present invention, the concentration of active intracellular PR ("PR" as used herein refers to HIV protease) that is produced during late-stages of viral replication, prior to virus budding and maturation, is limited, thus restricting processing of host factors that could increase viral cytopathic effects and lead to infected cell death. In contrast, the present compounds promote the desired phenotype by engaging peptidyl peptidase 8 (DPP8) and/or dipeptidyl peptidase 9. (DPP9), which have been shown to bind to the function to find domain (FIIND) of the pattern recognition receptors (PRRs) caspase recruitment domain family member 8 (CARD8) and nucleotide-binding domain leucine-rich repeat pyrin domain containing 1 (NLRP1) and restrain their formation of inflammasomes. As a result, PR processing of CARD8 and/or NLRP1 is able to activate inflammasome formation, resulting in cell death by pyroptosis. This effect can be blocked in the presence of a PR inhibitor such as indinavir, demonstrating the role of PR in the process. Additionally, treatment of HIV-infected primary CD4+ T-cells, but not uninfected cells, with the present compounds results in cleavage of gasdermin-D (GSDMD) and liberation of the N-terminal pore-forming domain, a downstream consequence of inflammasome activation, which further supports the role of HIV in the process.

The compounds presently disclosed herein have activity as DPP8 and DPP9 enzymatic inhibitors and may additionally disrupt complexes formed with CARD8 and/or NLRP1. The effects of engaging DPP8 and/or DPP9 on downstream CARD8 and/or NLRP1 inflammasome activation have been previously documented, often using the non-selective inhibitor of post-proline cleaving serine proteases Valboro-Pro (VbP) (Okondo, M C et al., DPP8 and DPP9 inhibition induces pro-caspase-1-dependent monocyte and macrophage pyroptosis, *Nat Chem Biol.* 2017, 13(1):46-53; Okondo M C et al., Inhibition of Dpp8/9 activates the Nlrp1b inflammasome, *Cell Chem Biol.* 2018, 25(3):262-267.c5; Zhong F L et al, Human DPP9 represses NLRP1 inflammasome and protects against autoinflammatory diseases via both peptidase activity and FIIND domain binding, *J Biol Chem,* 2018, 293(49): 18864-18878; de Vasconcelos N M et al., DPP8/DPP9 inhibition elicits canonical Nlrp1b inflammasome hallmarks in murine macrophages, Life Sci Alliance, 2019 Feb. 4, 2(1): e201900313; Griswold A R et al., DPP9's enzymatic activity and not its binding to CARD8 inhibits inflammasome activation, *ACS Chem Biol.* 2019, 14(11):2424-2429; Gai K et al., DPP8/9 inhibitors are universal activators of functional NLRP1 alleles, Cell Death Dis. 2019 Aug. 5, 10(8):587; Johnson D C et al., DPP8/9 inhibitors activate the CARD8 inflammasome in resting lymphocytes. Cell Death Dis. 2020 Aug. 14, 11(8):628; Taabazuing C Y et al., The NLRP1 and CARD8 inflammasomes, Immunol Rev. 2020 Sep, 297(1): 13-25; Linder A et al., CARD8 inflammasome activation triggers pyroptosis in human T cells. EMBO J., 2020 Oct. 1, 39(19):e105071; Chui A J et al., Activation of the CARD8 Inflammasome Requires a Disordered Region, Cell Rep., 2020 Oct. 13, 33(2): 108264; Sharif H et al., Dipeptidyl peptidase 9 sets a threshold for CARD8 inflammasome formation by sequestering its active C-terminal fragment, Immunity 2021 Jul. 13, 54(7): 1392-1404.e10; Huang M et al., Structural and biochemical mechanisms of NLRP1 inhibition by DPP9. Nature, 2021 Apr, 592(7856):773-777; Hollingsworth L R et al., DPP9 sequesters the C terminus of NLRP1 to repress inflammasome activation, Nature 2021 Apr, 592(7856):778-783; Sharif H et al., Dipeptidyl peptidase 9 sets a threshold for CARD8 inflammasome formation by sequestering its active C-terminal fragment, Immunity 2021 Jul. 13, 54(7): 1392-1404.e10.

Additionally, the ability of NLRP1 to sense and be activated by pathogens such as *Toxoplasma gondii* (Gov L et al., Human innate immunity to *Toxoplasma gondii* is mediated by host caspase-1 and ASC and parasite GRA15, MBio., 2013, 4(4):e00255; Ewald S E et al., NLRP1 is an inflammasome sensor for *Toxoplasma gondii*, Infect Immun. 2014, 82(1):460-468) and various viruses (Tsu B V et al. Diverse viral proteases activate the NLRP1 inflammasome, Elife., 2021 Jan. 7, 10:e60609.) or pathogen virulence factors, such as anthrax lethal toxin (Boyden E D et al., Nalp1b controls mouse macrophage susceptibility to anthrax lethal toxin, Nat Genet. 2006, 38(2):240-244; Newman Z L et al., Susceptibility to anthrax lethal toxin-induced rat death is controlled by a single chromosome 10 locus that includes rNlrp1, *PLOS Pathog*, 2010, 6(5):e1000906; Levinsohn J L et al. Anthrax lethal factor cleavage of Nlrp1 is required for activation of the inflammasome, PLoS Pathog., 2012, 8(3): e1002638; Chavarría-Smith J et al., Direct proteolytic cleavage of NLRP1b is necessary and sufficient for inflammasome activation by anthrax lethal factor, *PLOS Pathog.*, 2013, 9(6):e1003452) and the *Shigella flexneri* ubiquitin ligase secreted effector IpaH7.8 (Sandstrom A et al. Functional degradation: A mechanism of NLRP1 inflammasome activation by diverse pathogen enzymes, Science, 2019 Apr. 5, 364(6435): caau 1330) have been described. CARD8 was only recently reported to act as a pathogen sensor by Wang et al (Wang Q et al., CARD8 is an inflammasome sensor for HIV-1 protease activity, Science 2021 Mar. 19, 371(6535): cabe1707). The authors demonstrated that PR can cleave the N-terminus of CARD8, leading to liberation of the C-terminal domain, inflammasome assembly, and downstream pyroptotic cell death in macrophages and CD4+ T-cells. The authors propose "that enhancement of intracellular viral protease activity may be an effective strategy to clear residual HIV-1 in patients," which is consistent with an approach previously pursued using HIV TACK compounds that bind to the RT domain within HIV GAG-POL, induce dimerization and premature intracellular PR activation, and ultimately cause selective HIV-1 infected cell death, e.g., see WO2020/131597 and WO2020/236692. Hence, a complementary approach to activating CARD8 (and/or NLRP1) would be to engage the DPP8 and/or DPP9 proteins, reduce their restriction of CARD8 (and/or NLRP1) inflammasome activation, and increase the effect of PR-mediated inflammasome activation, such that even with the limited concentration of active intracellular PR that is produced during late-stages of viral replication there is death of HIV GAG-POL expressing cells. Indeed, we have observed synergy in accelerating the death of HIV GAG-POL expressing cells when testing the cyclohexylglycine derivatives in the present disclosure in combination with previously described TACK compounds targeting the RT domain within HIV GAG-POL.

Thus, new therapies that can selectively kill the HIV infected cells would provide new treatment options for HIV infection. Treatment with compounds that can accelerate death of HIV infected cells and decrease the overall number of virally infected cells that persist within patients has the potential to decrease residual viremia in HIV suppressed individuals and address co-morbidities associated with chronic viral infection such as chronic inflammation, immune dysfunction, accelerated aging, cardiovascular disease (CVD), central nervous system (CNS), and other tissue and end-organ damage. Furthermore, treatment with compounds that can purge the remaining HIV reservoir may prolong viral remission off therapy and play a role in an HIV cure strategy.

SUMMARY OF THE INVENTION

The present disclosure is directed to cyclohexylglycine derivatives and their use as HIV-infected cell kill agents which accelerate the death of HIV GAG-POL expressing cells without concomitant cytotoxicity to HIV naïve cells. Accordingly, the compounds disclosed herein are useful for the treatment or prophylaxis of infection by HIV, or for the treatment, prophylaxis or delay in the onset or progression of AIDS or AIDS Related Complex (ARC). Additionally, the compounds are useful for selectively killing HIV infected, GAG-POL expressing cells in a subject infected with HIV. Compositions and methods of use comprising the compounds of this disclosure are also provided.

DETAILED DESCRIPTION OF THE INVENTION

The present disclosure is directed to a compound of Formula I

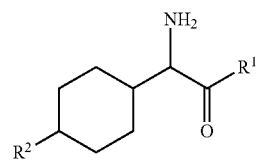

or a pharmaceutically acceptable salt thereof, wherein:
$R^1$ is selected from:

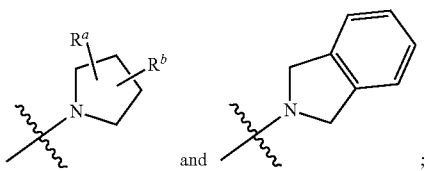

$R^a$ and $R^b$ are each independently selected from —H, halo or —C≡N;
$R^2$ is selected from —H, —OH, —O—$C_{1-3}$alkyl, or

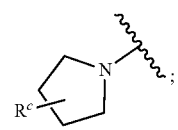

and
$R^c$ is selected from —H, —O—$(CH_2)_{1-3}$—C≡CH, or —O—$(CH_2)_{1-3}$—O—$(CH_2)_{1-3}$—C≡CH.

In an embodiment of this disclosure are compounds of Formula I, or pharmaceutically acceptable salts thereof, having structural Formula II:

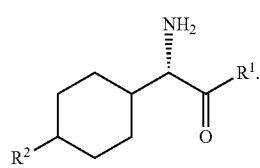

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). When the compounds of Formula I contain one or more acidic groups or basic groups, the invention includes the corresponding pharmaceutically acceptable salts.

Compounds of Formula I, which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

The instant disclosure encompasses any composition comprised of a compound of Formula I or a compound that is a salt thereof, including for example but not limited to, a composition comprised of said compound associated together with one or more additional molecular and/or ionic component(s) which may be referred to as a "co-crystal." The term "co-crystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals). There is no proton transfer between the dissimilar components and the solid phase is neither a simple salt nor a solvate. A discussion of co-crystals can be found, e.g., in S. Aitipamula et al., *Crystal Growth and Design*, 2012, 12(5), pp. 2147-2152.

Furthermore, compounds of the present disclosure may exist in amorphous form and/or one or more crystalline forms, and as such all amorphous and crystalline forms and mixtures thereof of the compounds of Formula I and salts thereof are intended to be included within the scope of the present disclosure. In addition, some of the compounds of the instant disclosure may form solvates with water (i.e., a hydrate) or common organic solvents. Such solvates and hydrates, particularly the pharmaceutically acceptable solvates and hydrates, of the compounds of this disclosure are likewise encompassed within the scope of the compounds defined by Formula I and the pharmaceutically acceptable salts thereof, along with un-solvated and anhydrous forms of such compounds.

Accordingly, the invention is directed to compounds of Formula I or salts thereof including pharmaceutically acceptable salts thereof, embodiments thereof and specific compounds described and claimed herein, encompass all possible stereoisomers, tautomers, physical forms (e.g., amorphous and crystalline forms), co-crystal forms, solvate and hydrate forms, and any combination of the foregoing forms where such forms are possible.

Another embodiment of the present disclosure is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as, high performance liquid chromatography, and/or mass spectrometry or NMR techniques. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual stereoisomer.

The compounds of Formula I herein, and pharmaceutically acceptable salts thereof, are useful for engaging DPP8 and/or DPP9 leading to PR-mediated inflammasome activation thereby selectively killing HIV infected GAG-POL expressing cells without concomitant cytotoxicity to HIV naïve cells, referred to herein as HIV-infected cell kill, or more specifically HIV-infected cell kill activity. Thus, the compounds of Formula I and pharmaceutically acceptable salts thereof are useful for:

(i) A method for the treatment or prophylaxis of infection by HIV, or for the treatment, prophylaxis, or delay in the onset or progression of AIDS or ARC in a human subject in need thereof which comprises administering to the human subject an effective amount of the compound according to Formula I, or a pharmaceutically acceptable salt thereof;

(ii) A method for engaging DPP8 and/or DPP9 in HIV-infected cells in a human subject in need thereof which comprises administering to the human subject an effective amount of the compound according to Formula I, or a pharmaceutically acceptable salt thereof;

(iii) A method for selectively killing HIV infected GAG-POL expressing cells without concomitant cytotoxicity to HIV naïve cells in a human subject which comprises administering to the human subject an effective amount of the compound according to Formula I, or a pharmaceutically acceptable salt thereof; and/or (iv) A method for augmenting the suppression of HIV viremia in a human subject whose viremia is being suppressed by administration of one or more compatible HIV antiviral agents, which comprises additionally administering to the human subject an effective amount of the compound according to Formula I, or a pharmaceutically acceptable salt thereof.

Additionally, the compounds of Formula I and pharmaceutically acceptable salts thereof are useful for any of the methods (i), (ii), (iii) or (iv) above, further comprising administering to the human subject an effective amount of one or more compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents. In the methods of (i), (ii) (iii) or (iv) immediately above, the human subject can be treated with a compound of Formula I or a pharmaceutically acceptable salt thereof in addition to treatment with one or more compatible HIV antiviral agents.

The compounds of Formula I and pharmaceutically acceptable salts thereof are also useful for a method for augmenting the suppression of HIV viremia in a human subject whose viremia is being suppressed by administration of one or more compatible HIV antiviral agents, which comprises additionally administering to the human subject an effective amount of the compound according to Formula I, or a pharmaceutically acceptable salt thereof.

Other embodiments of the present disclosure include the following:
(a) A pharmaceutical composition comprising an effective amount of a compound of Formula I or a pharmaceutically acceptable salt thereof, and a pharmaceutically acceptable carrier.
(b) A pharmaceutical composition which comprises the product prepared by combining (e.g., mixing) an effective amount of a compound of Formula I or a pharmaceutically acceptable salt thereof, and a pharmaceutically acceptable carrier.
(c) The pharmaceutical composition of (a) or (b), further comprising an effective amount of one or more compatible anti-HIV agents selected from the group consisting of HIV antiviral agents, immunomodulators, anti-infective agents and latency reversing agents.
(d) The pharmaceutical composition of (c), wherein the compatible anti-HIV agent is selected from one or more of an antiviral selected from the group consisting of nucleoside or nucleotide HIV reverse transcriptase inhibitors, nucleoside HIV reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.
(e) A combination which is (i) a compound of Formula I or a pharmaceutically acceptable salt thereof and (ii) one or more compatible anti-HIV agents selected from the group consisting of HIV antiviral agents, immunomodulators, anti-infective agents and latency reversing agents; wherein the compound and the compatible anti-HIV agent are each employed in an amount that renders the combination effective for the treatment or prophylaxis of infection by HIV, or for the treatment, prophylaxis or delay in the onset or progression of AIDS or ARC.
(f) The combination of (e), wherein the compatible anti-HIV agent is an antiviral selected from the group consisting of nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.
(g) A method for engaging DPP8 and/or DPP9 in HIV-infected cells, a method for selectively killing HIV infected GAG-POL expressing cells without concomitant cytotoxicity to HIV naïve cells, and/or a method for the treatment or prophylaxis of infection by HIV, or for the treatment, prophylaxis, or delay in the onset or progression of AIDS or ARC, comprising administering an effective amount of a compound of Formula I or a pharmaceutically acceptable salt thereof to a subject in need of such treatment.
(h) The method of (g), wherein the compound of Formula I or a pharmaceutically acceptable salt thereof is administered in combination with an effective amount of at least one other compatible HIV antiviral selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.
(i) The method of (g) or (h) comprising administering to the subject the pharmaceutical composition of (a), (b), (c) or (d) or the combination of (c) or (f).
(j) Use of a compound of Formula I or a pharmaceutically acceptable salt thereof in the manufacture of a medicament for (1) engaging DPP8 and/or DPP9 in HIV-infected cells in a subject; (2) selectively killing HIV infected GAG-POL expressing cells without concomitant cytotoxicity to HIV naïve cells in a subject; (3) treatment or prophylaxis of infection by HIV in a subject; (4) treatment, prophylaxis or delay in the onset or progression of AIDS or ARC in a subject; (5) augmenting the suppression of HIV viremia in a subject undergoing treatment with a compatible anti-HIV agent, and/or (6) augmenting the suppression of HIV viremia in a subject whose viremia is being suppressed by administration of one or more compatible HIV antiviral agents.
(k) A compound of Formula I, or a pharmaceutically acceptable salt thereof, for use in (1) engaging DPP8 and/or DPP9 in HIV-infected cells; (2) selectively killing HIV infected GAG-POL expressing cells without concomitant cytotoxicity to HIV naïve cells; (3) treatment or prophylaxis of infection by HIV; (4) the treatment, prophylaxis or delay in the onset or progression of AIDS or ARC; and/or (5) augmenting the suppression of HIV viremia in a subject undergoing treatment with a compatible anti-HIV agent, and/or (6) augmenting the suppression of HIV viremia in a subject whose viremia is being suppressed by administration of one or more compatible HIV antiviral agents.

Additional embodiments of the present invention include each of the pharmaceutical compositions, methods and uses set forth in the preceding paragraphs, wherein the compound of Formula I or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se.

In another embodiment of the present disclosure are the pharmaceutical compositions, methods, medicaments, uses and combinations set forth herein, wherein the HIV of interest is HIV-1. Thus, for example, in any of the pharmaceutical compositions, methods, medicaments, uses and combinations using the compounds of Formula I or pharmaceutically acceptable salts thereof, the compound or salt thereof is employed in an amount effective against HIV-1; and when used in combination with one or more compatible anti-HIV agent(s), each such additional agent is a compatible HIV-1 antiviral selected from, for example but not limited to, one or more of nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

The term "administration" and variants thereof (e.g., "administering" a compound) in reference to a compound of Formula I means providing the compound to the individual in need of treatment or prophylaxis and includes both self-administration and administration to the patient by another person or any other means. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

The term "subject" or "patient" as used herein refers to a human (or "person") who has been the object of treatment, observation or experiment. Examples of patients to be treated with an HIV-infected cell kill agent include but are not limited to, patients who have been infected with HIV, and/or HIV infected patients whose HIV viral load has been suppressed and/or is considered to be undetectable at time of HIV-infected cell kill treatment. Patients to be treated with an HIV-infected cell kill agent also include, but are not limited to, those using an HIV-infected cell kill agent for prophylaxis of HIV infection or for post-exposure prophylaxis after being potentially exposed to HIV to prevent becoming infected.

"Prophylaxis" includes each of pre-exposure prophylaxis (PrEP), i.e., using a compound of Formula I or a pharmaceutically acceptable salt thereof to prevent HIV infection in a person who does not have HIV, and post-exposure prophylaxis (PEP), i.e., using a compound of Formula I or a pharmaceutically acceptable salt thereof after being potentially exposed to HIV to prevent becoming infected with HIV.

The term "effective amount" as used herein means an amount of a compound sufficient to engage DPP8 and/or DPP9 in HIV-infected cells and selectively kill HIV infected GAG-POL expressing cells without concomitant cytotoxicity to HIV naïve cells; and/or exert a therapeutic effect, and/or exert a prophylactic effect after administration. One embodiment of "effective amount" is a "therapeutically effective amount" which is an amount of a compound that is effective for selectively killing HIV infected GAG-POL expressing cells, effective for treating HIV infection, or effective for the treatment, prophylaxis or delay in the onset or progression of AIDS or ARC in a patient infected with HIV. Another embodiment of "effective amount" is a "prophylactically effective amount" which is an amount of the compound that is effective for prophylaxis of HIV infection, or prophylaxis of AIDS or ARC in an HIV-infected patient. It is understood that an effective amount can simultaneously be both a therapeutically effective amount, e.g., for treatment of HIV infection, and a prophylactically effective amount, e.g., for prevention or reduction of risk for developing AIDS or ARC in a subject infected with HIV.

In the combination therapies of the present invention, an effective amount can refer to each individual agent or to the combination as a whole, wherein the amounts of all agents administered in the combination are together effective, but wherein a component agent of the combination may or may not be present individually in an effective amount with reference to what is considered effective for that component agent if it were administered alone.

In the methods of the present invention., (i.e., selectively killing HIV infected GAG-POL expressing cells, the treatment of infection by HIV, prophylaxis of HIV infection or the treatment, prophylaxis or delay in the onset or progression of AIDS or ARC and other methods described herein), the compounds of this invention, or salts thereof, can be administered by means that produce contact of the active agent with the agent's site of action. They can be administered by conventional means available for use in conjunction with pharmaceuticals, either as individual therapeutic agents or in a combination of therapeutic agents. The compound can be administered itself, but typically is administered with a pharmaceutical carrier selected on the basis of the chosen route of administration and standard pharmaceutical practice. The compounds of the invention can, for example, be administered orally (e.g., via tablet or capsule), parenterally (including subcutaneous injections, intravenous, intramuscular or intrasternal injection, or infusion techniques), by inhalation spray, or rectally, in the form of a unit dosage of a pharmaceutical composition containing an effective amount of the compound and conventional non-toxic pharmaceutically acceptable carriers, adjuvants and vehicles. The compound could also be administered via an implantable drug delivery device adapted to provide an effective amount of the compound or a pharmaceutical composition of the compound over an extended period of time.

Formulations

Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Implantable compositions can be prepared according to methods known in the art wherein the carrier comprises the active chemical ingredient with polymers and suitable excipients, or utilizing an implantable device for drug delivery. Further description of methods suitable for use in preparing pharmaceutical compositions for use in the present invention and of ingredients suitable for use in said compositions is provided in Remington—The Science and Practice of Pharmacy, 22nd Edition, published by Pharmaceutical Press and Philadelphia College of Pharmacy at University of the Sciences, 2012, ISBN 978 0 85711-062-6 and prior editions.

Formulations of compounds of Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are known in the art. For example, solid dispersions can be prepared using excipients and processes as described in reviews (e.g., A. T. M. Serajuddin, J Pharm Sci, 88:10, pp. 1058-1066 (1999)). Nanoparticulate systems based on both attrition and direct synthesis have also been described in reviews such as Wu et al (F. Kesisoglou, S. Panmai, Y. Wu, Advanced Drug Delivery Reviews, 59:7 pp. 631-644 (2007)).

The compounds of Formula I may be administered in a dosage range of, e.g., 1 to 20 mg/kg, or 1 to 10 mg/kg, or about 5 mg/kg of mammal (e.g., human) body weight per day, or at other time intervals as appropriate, in a single dose or in divided doses. The compounds of Formula I may be administered in a dosage range of 0.001 to 2000 mg. per day in a single dose or in divided doses. Examples of dosage ranges are 0.01 to 1500 mg per day, or 0.1 to 1000 mg per day, administered orally or via other routes of administration in a single dose or in divided doses.

For oral (e.g., tablets or capsules) or other routes of administration, the dosage units may contain 100 mg to 1500 mg of the active ingredient, for example but not limited to, 100, 150, 200, 250, 300, 350, 400, 450, 500, 600, 700, 800, 900, 1000, 1100, 1200, 1300, 1400 or 1500 milligrams of the active ingredient for the symptomatic adjustment of the dosage to the patient to be treated. Furthermore, the compound may be formulated in oral formulations for immediate or modified release such as extended or controlled release. When the compound of Formula I is administered as a salt, reference to an amount of the compound in milligrams or grams is based on the free form (i.e., the non-salt form) of the compound.

Daily administration can be via any suitable route of administration but is preferably via oral administration and can be a single dose or more than one dose at staggered times (divided daily doses) within each 24-hour period. Each dose may be administered using one or multiple dosage units as appropriate.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given dose. The amount and frequency of administration will be regulated according to the judgment of the attending clinician considering such factors.

An "anti-HIV agent" is any agent which is directly or indirectly effective in the inhibition of HIV, the treatment or prophylaxis of HIV infection, and/or the treatment, prophylaxis or delay in the onset or progression of AIDS or ARC. It is understood that an anti-HIV agent is effective in treating, preventing, or delaying the onset or progression of HIV infection or AIDS and/or diseases or conditions arising therefrom or associated therewith. The present disclosure is additionally directed to use of a compound of Formula I or pharmaceutically acceptable salts thereof, with one or more compatible anti-HIV agents, i.e., anti-HIV agents, excluding HIV protease inhibitors (also referred to as "compatible HIV antivirals"). For example, the compounds of Formula I may be administered in combination with effective amounts of one or more compatible anti-HIV agents selected from HIV antiviral agents, immunomodulators, anti-infectives, or vaccines useful for treating HIV infection or AIDS. Suitable compatible HIV antivirals for use in combination with the compounds of the present disclosure include, but are not limited to, those listed in Table A as follows:

TABLE A

| Antiviral Agents for Treating HIV infection or AIDS | |
|---|---|
| Name | Type |
| abacavir, ABC, ZIAGEN ® | NRTI |
| abacavir + lamivudine, EPZICOM ® | NRTI |
| abacavir + lamivudine + zidovudine, TRIZIVIR ® | NRTI |
| AZT, zidovudine, azidothymidine, RETROVIR ® | NRTI |
| bictegravir | InSTI |
| bictegravir + tenofovir alafenamide fumarate + emtricitabine, BIKTARVY ® | InSTI/NRTI/NRTI |
| capravirine | NNRTI |
| cabotegravir | InSTI |
| Cabotegravir + rilpivirine, CABENUVA | InSTI/NNRTI |
| ddC, zalcitabine, dideoxycytidine, HIVID ® | NRTI |
| ddI, didanosine, dideoxyinosine, Videx ® | NRTI |
| ddI (enteric coated), VIDEX EC ® | NRTI |
| delavirdine, DLV, RESCRIPTOR ® | NNRTI |
| Dolutegravir + lamivudine, DOVATO ® | InSTI/NRTI |
| Dolutegravir + rilpivirine, JULUCA ® | InSTI/NNRTI |
| dolutegravir, TIVICAY ® | InSTI |
| dolutegravir + abacavir + lamivudine, TRIUMEQ ® | InSTI/NRTI/NRTI |
| doravirine, PIFELTRO ™ | NNRTI |

TABLE A-continued

Antiviral Agents for Treating HIV infection or AIDS

| Name | Type |
| --- | --- |
| doravirine/lamivudine/tenofovir disoproxil fumarate, DELSTRIGO ™ | NNRTI/NRTI/NRTI |
| efavirenz, EFV, SUSTIVA ®, STOCRIN ® | NNRTI |
| Efavirenz/emtricitabine/tenofovir disoproxil fumarate, ATRIPLA ® | NNRTI/NRTI/NRTI |
| Islatravir, (4'-ethynyl-2-fluoro-2'-deoxyadenosine; EFdA) | NRTTI |
| Elvitegravir, VITEKTA ® | InSTI |
| emtricitabine, FTC, EMTRIVA ® | NRTI |
| emtricitabine + tenofovir alafenamide fumarate, DESCOVY ® | NRTI/NRTI |
| emtricitabine + tenofovir disoproxil fumarate, TRUVADA ® | NRTI/NRTI |
| emivirine, COACTINON ® | NNRTI |
| enfuvirtide, FUZEON ® | FI |
| enteric coated didanosine, VIDEX EC ® | NRTI |
| etravirine, TMC-125 | NNRTI |
| Fostemsavir, RUKOBIA ® | AI |
| Ibalizumab-uiyk (TROGARZO ®) | Post-Attachment Inhibitor or Monoclonal Antibody |
| lamivudine, 3TC, EPIVIR ® | NRTI |
| lamivudine + zidovudine, COMBIVIR ® | NRTI/NRTI |
| lenacapavir | Capsid inhibitor |
| maraviroc, SELZENTRY ® | EI |
| nevirapine, NVP, VIRAMUNE ® | NNRTI |
| raltegravir, ISENTRESS ™ | InSTI |
| rilpivirine, EDURANT ® | NNRTI |
| stavudine, d4T, didehydrodeoxythymidine, ZERIT ® | NRTI |
| tenofovir disoproxil fumarate (TDF), VIREAD ® | NRTI |
| tenofovir alafenamide fumarate (TAF) | NRTI |
| vicriviroc | EI |

AI = attachment inhibitor; EI = entry inhibitor; FI = fusion inhibitor; InSTI = integrase inhibitor; NRTI = nucleoside or nucleotide reverse transcriptase inhibitor; NNRTI = non-nucleoside reverse transcriptase inhibitor; NRTTI = nucleoside reverse transcriptase translocation inhibitor. Some of the drugs listed in Table A are used in a salt form; e.g., abacavir sulfate, delavirdine mesylate.

The HIV-infected cell kill effect elicited by an HIV-infected cell kill agent depends on intracellular activity of PR. Therefore additional active agents that increase the amount and/or activity of intracellular PR in infected cells—such as NNRTIs that bind to immature RT within the GAG-POL polyprotein, enhance dimerization, and prematurely activate PR intracellularly—when used together with HIV-infected cell kill therapy are likely to enhance the HIV-infected cell kill effect. The present disclosure is additionally directed to use of a compound of Formula I, or a pharmaceutically acceptable salt thereof, with one or more additional agents increasing the amount and/or activity of intracellular PR. For example, the compounds of Formula I may be administered in combination with effective amounts of one or more agents that increase the amount and/or activity of intracellular PR for treatment of HIV infection or AIDS. Examples of agents that increase the amount and/or activity of intracellular PR for use in combination with the compounds of the present disclosure include, but are not limited to NNRTIs, such as EFV and RPV, and HIV TACK agents.

Thus, the compounds of Formula I, or pharmaceutically acceptable salts thereof, used together with an agent that increases the amount and/or activity of intracellular PR can be useful for:
  (i) A method for increasing the amount and/or activity of intracellular PR and engaging DPP8 and/or DPP9 in HIV-infected cells (e.g., CD4 T cells) in a human subject which comprises administering to the subject an effective amount of a compound according to Formula I, or a pharmaceutically acceptable salt thereof, and an agent that increases the amount and/or activity of intracellular PR; and/or
  (ii) A method for increasing the amount and/or activity of intracellular PR and selectively killing HIV-infected GAG-POL expressing cells (e.g., latently HIV-infected CD4 T cells or central memory CD4 T cells), without concomitant cytotoxicity to HIV naïve cells, in a human subject which comprises administering to the subject an effective amount of a compound according to Formula I, or a pharmaceutically acceptable salt thereof, and an agent that increases the amount and/or activity of intracellular PR.

The HIV-infected cell kill effect elicited by an HIV-infected cell kill agent depends on expression of viral GAG-POL. Therefore additional active agents, such as latency reversing agents ("LRA" or "LRAs"), that enhance GAG-POL production in infected cells and/or activate viral expression in cells that comprise the latent HIV reservoir, when used together with HIV-infected cell kill therapy, are likely to enhance the HIV-infected cell kill effect. The present disclosure is additionally directed to use of a compound of Formula I, or a pharmaceutically acceptable salt thereof, with one or more LRA(s). For example, the compounds of Formula I may be administered in combination with effective amounts of one or more LRA(s) for treatment of HIV infection or AIDS. Examples of LRAs for use in combination with the compounds of the present disclosure include, but are not limited to epigenetic modifiers such as histone deacetylase (HDAC) inhibitors, DNA methyltransferase (DNMT) inhibitors, and histone methyltransferase (HMT) inhibitors; Protein Kinase C (PKC) agonists such as prostratins, bryostatins, or ingenols; inducers of P-TEFb release such as BET inhibitors (e.g., JQ1 or a class of drugs that reversibly bind the bromodomains of Bromodomain and Extra-Terminal motif (BET) proteins BRD2, BRD3, BRD4, and/or BRDT), antagonists of C—C chemokine receptor type 5 (CCR5), inducers of non-canonical NF-κB pathway (e.g., second mitochondria-derived activator of caspases (SMAC) mimetics or inhibitor of apoptosis proteins (IAP) antagonists, proteasome inhibitors, toll-like receptor (TLR) agonists, mitogen-activated protein kinase (MAPK) agonists, Ak strain transforming/protein kinase B (AKT/PKB) pathway activators, cytokines and immunomodulatory agents such as immune checkpoint inhibitors and those described elsewhere such as Bullen et al, Nature Medicine, 20:425-429 (2014); Ait-Ammar et al, Frontiers in Microbiology, 10:3060 (2019); and Fujinaga et al, Viruses. 12:11 (2020).

Examples of HDAC inhibitors that can be used as latency reversing agents include, but are not limited to, vorinostat, panabinostat, romidepsin, and valproic acid. Examples of DNMT inhibitors that can be used as latency reversing agents include, but are not limited to, 5-aza-2'-cytidine and 5-aza-2'-deoxycytidine. Examples of HMT inhibitors that can be used as latency reversing agents include, but are not limited to, chaetocin, 3-deazaneplanocin A, tazemetostat (EPZ-6438), N-[(1,2-dihydro-6-methyl-2-oxo-4-propyl-3-pyridinyl)methyl]-1-(1-methylethyl)-6-[2-(4-methyl-1-piperazinyl)-4-pyridinyl]-1H-indazole-4-carboxamide (GSK-343) and 2-cyclohexyl-6-methoxy-N-[1-(1-methylethyl)-4-piperidinyl]-7-[3-(1-pyrrolidinyl)propoxy]-4-quinazolinamine (UNC-0638). Examples PKC agonists that can be used as latency reversing agents include, but are not limited to, phorbolesters such as prostratin and phorbol myristate acetate (PMA), bryostatin-1, and ingenol. Examples of BET inhibitors that can be used as a latency reversing agents include, but are not limited to, JQ1 ((S)-tert-butyl 2-(4-(4-chlorophenyl)-2,3,9-trimethyl-6H-thieno[3,2-f][1,2,4]triazolo[4,3-a][1.4]diazepin-6-yl)acetate), iBET, and N-cyclohexyl-2-(4-(3,5-dimethylisoxazol-4-yl)-2-methoxyphenyl)imidazo[1,2-a]pyrazin-3-amine (UMB-136). An example of a CCR5 antagonist that can be used as latency reversing agent includes, but is not limited to, maraviroc. Examples of inducers of the non-canonical NF-κB pathway and SMAC mimetics/IAP inhibitors that can be used as latency reversing agents include, but are not limited to, 3,3'-[2,4-hexadiyne-1,6-diylbis[oxy[(1S,2R)-2,3-dihydro-1H-indene-2,1-diyl]]]bis[N-methyl-L-alanyl-(2S)-2-cyclohexylglycyl-L-prolinamide (AZD5582), Ciapavir, Birinapant, LCL161, and DEBIO1143/AT-406. Examples of proteasome inhibitors that can be used as latency reversing agents include, but are not limited to, bortezomib and ixazomib. Examples of TLR agonists that can be used as latency reversing agents include, but are not limited to, the TLR2 agonist Pam3CSK4, the TLR7 agonist vesatolimod, and the TLR9 agonists Lefitolimod (MGN1703) and CPG 7909. An example of an MAPK agonist that can be used as a latency reversing agent includes, but is not limited to, procyanidin trimer C1. An example of an AKT pathway activator that can be used as latency reversing agent includes, but is not limited to, disulfiram. Examples of immunomodulatory cytokines that can be used as latency reversing agents include, but are not limited to, IL-2, IL-7, and IL-15, including the IL-15 superagonist N-803. Examples of immune checkpoint inhibitors include, but are not limited to, inhibitors of Programmed cell death protein 1 (PD1), Programmed death-ligand 1 (PD-L1) inhibitors, cytotoxic T-lymphocyte-associated protein 4 (CTLA-4), Lymphocyte-activation gene 3 (LAG3), T cell immunoreceptor with Ig and ITIM domains) (TIGIT) and CD24Fc, a recombinant fusion protein composed of the extracellular domain of the mature human glycoprotein cluster of differentiation 24 (CD24) linked to a human immunoglobulin G1 (IgG1) Fc domain.

Thus, the compounds of Formula I, or pharmaceutically acceptable salts thereof, used together with a latency reversing agent can be useful for:

(i) A method for re-activating latent HIV and eliciting GAG-POL dimerization in HIV-infected cells (e.g., CD4 T cells) in a human subject which comprises administering to the subject an effective amount of a compound according to Formula I, or a pharmaceutically acceptable salt thereof, and a latency reversing agent; and/or (ii) A method for re-activating latent HIV and selectively killing HIV-infected GAG-POL expressing cells (e.g., latently HIV-infected CD4 T cells or central memory CD4 T cells), without concomitant cytotoxicity to HIV naïve cells, in a human subject which comprises administering to the subject an effective amount of a compound according to Formula I, or a pharmaceutically acceptable salt thereof, and a latency reversing agent.

Compounds of this invention can be used in combination with any one or more of antiviral agents, e.g. but not limited to those listed in Table A, and/or one or more agents that increase the amount and/or activity of intracellular PR e.g. but not limited to, the agents that increase the amount and/or activity of intracellular PR described herein, and/or any one or more of LRAs, e.g. but not limited to, the LRAs described herein.

It is understood that the scope of combinations of the compounds of this invention with compatible anti-HIV agents is not limited to the HIV antivirals listed in Table A, but includes in principle any combination with any pharmaceutical composition useful for the treatment or prophylaxis of HIV AIDS, or ARC, with the exception of HIV protease inhibitors. The compatible HIV antiviral agents and other active agents will typically be employed in these combinations in their conventional dosage ranges and regimens as reported in the art, including, for example, the dosages described in the current Physicians' Desk Reference, Thomson P D R, 70th edition (2016), Montvale, NJ: PDR Network, or in prior editions thereof. The dosage ranges for a compound of the disclosure in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other DPP8 and/or DPP9 engagers, e.g., by competitive binding.

Compound Preparation

All reactions were performed under nitrogen atmosphere in round bottomed flasks. Proton NMR spectra were recorded on Varian Unity 400 or VRX-400 spectrometers (400 MHZ), a Varian Unity or Varian Plus (500 MHZ) spectrometer, or a Bruker AVANCE III HD 700 (700 MHZ) spectrometer. Chemical shifts are reported in parts per million (δ) downfield from tetramethylsilane as an internal standard. Samples were dissolved in acetonitrile:water or used as provided, and ionized by use of electrospray ionization (ESI) yielding [M+H]. External calibration was accomplished with oligomers of polypropylene glycol (PPG, average molecular weight 425 Da). Column chromatography was performed on ISCO Combiflash purification systems employing Silicycle prepacked silica gel cartridges and analytical thin layer chromatography was performed on EM Science Kieselgel 60 F254 plates. Solvents and reagents were obtained from commercial sources and used without further purification. The reported yields are the actual isolated yields of purified material and are not optimized.

Example 1

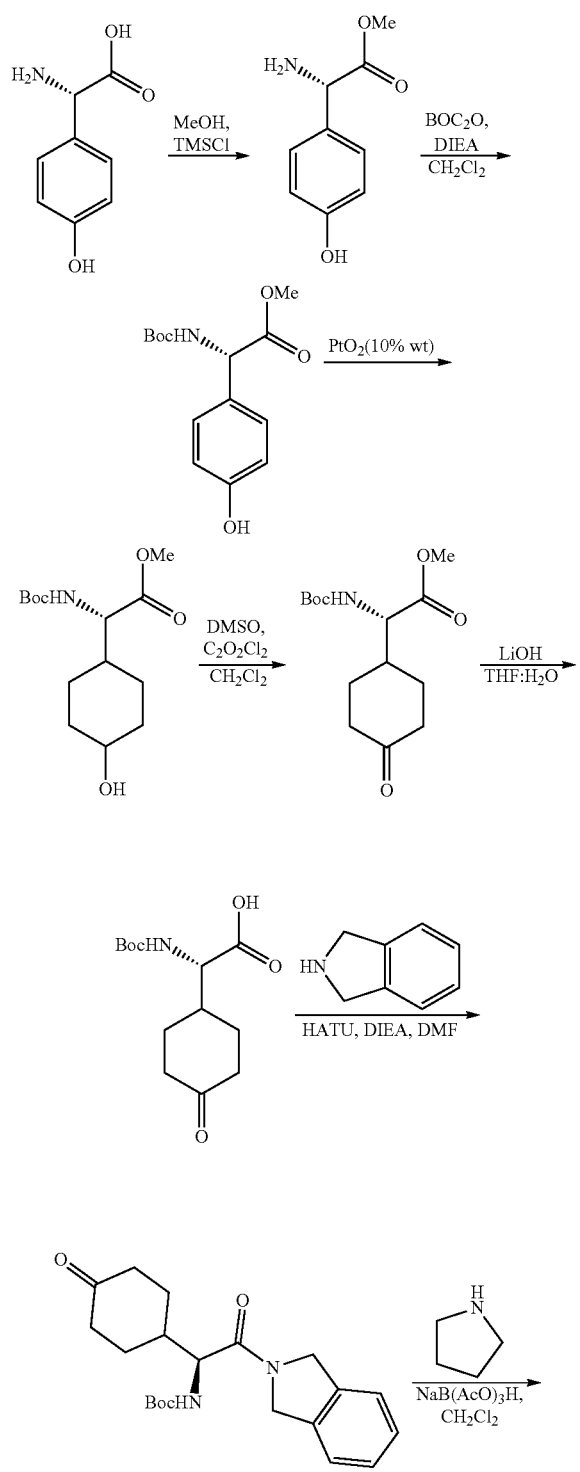

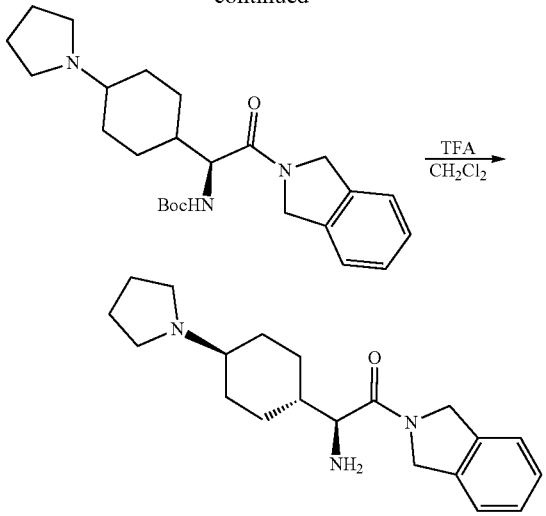

Step 1: Preparation of (2S)-2-amino-1-(1,3-dihydroisoindol-2-yl)-2-[(1R,4S)-4-(pyrrolidin-1-yl)cyclohexyl]ethenone Into a 5-L 4-necked round-bottom flask purged and maintained with an inert atmosphere of nitrogen, was placed MeOH (1.7 L), oxfenicine (170 g, 1.02 mol), and then chlorotrimethylsilane (221 g, 2.03 mol) was added dropwise with stirring at 25° C. The resulting solution was stirred for 16 hours at room temperature, concentrated in vacuo, providing the titled compound (180 g) as a solid.

Step 2: Preparation of methyl (2S)-2-[(tert-butoxycarbonyl)amino]-2-(4-hydroxyphenyl)acetate Into a 5 L 4-necked round-bottom flask purged and maintained with an inert atmosphere of nitrogen, was placed methyl (2S)-2-amino-2-(4-hydroxyphenyl)acetate (180 g, 993 mmol) in dichloromethane (2 L), di-tert-butyl dicarbonate (282 g, 1.29 mol, 1.3 equiv), followed by the addition of N,N-diisopropylethylamine (192 g, 1.49 mol, 1.5 equiv) dropwise with stirring at ambient temperature. The resulting solution was stirred for 16 hours treated with water (1 L), and extracted with dichloromethane (2×700 mL). The organic extracts were combined, dried with magnesium sulfate, filtered, and concentrated in vacuo. The reside was purified by crystallization from n-Hexane, providing the titled compound (255 g) as a solid.

Step 3: Preparation of methyl (2S)-2-[(tert-butoxycarbonyl)amino]-2-(4-hydroxycyclohexyl)acetate Into a 5 L sealed tube purged and maintained with an inert atmosphere of hydrogen (50 atm) was placed methyl (2S)-2-[(tert-butoxycarbonyl)amino]-2-(4-hydroxyphenyl)acetate (255 g, 906 mmol), PtO₂ (25 g, 10% wt/wt), and acetic acid (2.55 L). The resulting solution was stirred for 5 hours at ambient temperature, then partially concentrated, filtered, and the pH was adjusted to pH 10 with aqueous sodium bicarbonate (1M). The resulting mixture was extracted with ethyl acetate (3×200 mL) and the combined organic extracts were dried with sodium sulfate, filtered, and concentrated in vacuo. The residue was purified by silica gel column chromatography (eluting with ethyl acetate/hexane; 1:10), providing the titled compound (110 g) as an oil.

Step 4: Preparation of methyl (2S)-2-[(tert-butoxycarbonyl)amino]-2-(4-oxocyclohexyl)acetate Into a 3 L 4-necked round-bottom flask purged and maintained with an inert atmosphere of nitrogen, was placed a solution of oxalyl chloride (91.3 g, 719 mmol, 1.88 equiv) in dichloromethane (1 L) and cooled to −78° C. A solution of dimethylsulfoxide (109 g. 1.4 mol, 3.66 equiv) in dichloromethane (200 mL) was added dropwise and the resulting solution was stirred for 30 minutes, and then treated with a solution of methyl (2S)-2-[(tert-butoxycarbonyl)amino]-2-(4-hydroxycyclohexyl)acetate (110 g, 383 mmol, 1.0 equiv) in dichloromethane (300 mL) dropwise while stirring at −78° C. The resulting solution was aged for 1 hour, then treated with triethylamine (310 g, 3.06 mol, 8 equiv) dropwise. The mixture was warmed to −20° C. and then treated with water. The mixture was extracted with ethyl acetate (3×500 mL) and the combined organic extracts were combined, dried with magnesium sulfate, filtered, and concentrated in vacuo. The residue was purified via silica gel chromatography (eluting with ethyl acetate/hexane; 1:10), providing the partially purified titled compound as a solid (100 g).

Step 5: Preparation of (S)-[(tert-butoxycarbonyl)amino](4-oxocyclohexyl)acetic acid Into a 2 L 3-necked round-bottom flask purged and maintained with an inert atmosphere of nitrogen, was placed methyl (2S)-2-[(tert-butoxycarbonyl)amino]-2-(4-oxocyclohexyl)acetate (100 g, 350 mmol, 1.00 equiv) in tetrahydrofuran (1.0 L). The mixture was cooled to 0° C., treated with lithium hydroxide (16.8 g. 701 mmol, 2.0 equiv), and stirred for 3 hours. The mixture was treated with water (500 mL) and the pH of the solution was adjusted to pH 3 with hydrochloric acid (1 M aqueous). The resulting solution was extracted with ethyl acetate (2×200 mL) and the combined organic extracts were dried with magnesium sulfate, filtered, and concentrated in vacuo. The residue was purified by crystallization from n-hexane, providing the titled compound as a solid. (5V). This provided the title compound (95.0 g, over 2 steps).

Step 6: Preparation of tert-butyl N-[(1S)-2-(1,3-dihydroisoindol-2-yl)-2-oxo-1-(4-oxocyclohexyl)ethyl]carbamate Into a 2 L 4-necked round-bottom flask purged and maintained with an inert atmosphere of nitrogen, was placed (S)-[(tert-butoxycarbonyl)amino](4-oxocyclohexyl)acetic acid (95.0 g, 350 mmol, 1.0 equiv) in N,N-dimethylformamide (950 mL), isoindoline hydrochloride (59.9 g. 385 mmol, 1.1 equiv), and (1-[Bis(dimethylamino)methylene]-1H-1,2,3-triazolo[4,5-b]pyridinium 3-oxide hexafluorophosphate (173 g, 455 mmol, 1.3 equiv). The mixture was cooled to 0° C. and treated with N,N-diisopropylethylamine (181 g, 1.40 mol, 4 equiv) dropwise. The mixture was warmed to ambient temperature and stirred for 3 hours. The mixture was poured into water (5 L) and extracted with ethyl acetate (5×200 mL). The combined organic extracts were dried with magnesium sulfate, filtered, and concentrated in vacuo. The residue was purified by silica gel chromatography (eluting with ethyl acetate:petroleum ether; 1:1), providing the titled compound (100 g) as a foam.

Step 7: Preparation of tert-butyl N-[(1S)-2-(1,3-dihydroisoindol-2-yl)-2-oxo-1-[4-(pyrrolidin-1-yl)cyclohexyl]ethyl]carbamate Into a 2-L 4-necked round-bottom flask purged and maintained with an inert atmosphere of nitrogen, tert-butyl N-[(1S)-2-(1,3-dihydroisoindol-2-yl)-2-oxo-1-(4-oxocyclohexyl)ethyl]carbamate (100 g, 268 mmol) was dissolved in dichloromethane (1 L), treated with pyrrolidine (38.2 g, 536 mmol, 2.0 equiv) and cooled to 0° C. The mixture was treated portionwise with bis(acetyloxy)boranyl acetate sodium (113 g, 537 mmol, 2.0 equiv) and was aged an additional 2 hours. The mixture was treated with water and concentrated in vacuo. The residue was purified by preparative HPLC [C18 silica gel; mobile phase (0.5% TFA/$H_2O$): acetonitrile (85:15 to 55:45)]. The fractions were concentrated in vacuo, providing the titled compound as a grey solid (120 g).

Step 8: Preparation of (2S)-2-amino-1-(1,3-dihydroisoindol-2-yl)-2-[(1R,4S)-4-(pyrrolidin-1-yl)cyclohexyl]ethanone Into a 2-L 4-necked round-bottom flask purged and maintained with an inert atmosphere of nitrogen, tert-butyl N-[(1S)-2-(1,3-dihydroisoindol-2-yl)-2-oxo-1-[4-(pyrrolidin-1-yl)cyclohexyl]ethyl]carbamate (120 g, 221 mmol, 1.0 equiv) was dissolved in dichloromethane (360 mL), cooled to 0° C., and was treated with trifluoroacetic acid (360 mL). The mixture was warmed to ambient temperature, aged for 2 hours, and then concentrated in vacuo. The residue was partitioned between aqueous sodium bicarbonate and ethyl acetate. The organic layer was dried with magnesium sulfate, filtered, and concentrated in vacuo. The residue was purified by preparative SFC (CHIRALPAK AD-H; mobile phase ($CO_2$:MeOH=60:40)) providing the titled compound (10.1 g,) as a solid). High resolution mass spectrometry (ES+) m/z 328.2388 (M+H)+; [(M+H)+; calculated for $C_{20}H_{30}N_3O$, 328.2383]; $^1$H NMR (400 MHZ, Methanol-$d^4$): δ 7.34 (q, J=3.1 Hz, 4H), 5.08-4.89 (m 2H), 4.85-4.69 (m, 2H), 3.51 (d, J=6.7 Hz, 1H), 2.70 (d, J=6.0 Hz, 4H), 2.27-1.97 (m, 4H), 1.91-1.79 (m, 4H), 1.80-1.70 (m, 1H), 1.63 (dtd, J=11.5, 7.4, 3.2 Hz, 1H), 1.43-1.07 (m, 4H) ppm.

The compounds in Table 1 can be prepared by one skilled in the art using the above procedures.

TABLE 1

| Ex. No. | Compound Structure | HRMS [M + H]+ |
|---|---|---|
| 2 | (structure: 4-hydroxycyclohexyl amino acetyl isoindoline) | $C_{16}H_{23}N_2O_2$ calc'd 275.1754 observed 275.1765 |

1H NMR (500 MHz, CDCl3): δ 7.36-7.29 (m, 4H), 5.00-4.87 (m, 3H), 4.83 (d, J = 15.8 Hz, 1H), 4.08 (s, 1H), 3.46 (d, J = 6.8 Hz, 1H), 1.87 (d, J = 7.3 Hz, 1H), 1.79 (d, J = 12.1 Hz, 1H), 1.72-1.59 (m, 3H), 1.57 (d, J = 9.1 Hz, 2H), 1.49 (m, 1H), 1.28 (s, 1H), 0.94-0.87 (m, 1H) ppm

| 3 | (structure: cyclohexyl amino acetyl isoindoline) | $C_{16}H_{23}N_2O$ calc'd 259.1805 observed 259.1813 |
|---|---|---|

1H NMR (500 MHz, CDCl3): δ 7.34-7.25 (m, 4H), 4.94 (d, J = 13.3 Hz, 1H), 4.91-4.84 (m, 2H), 4.80 (d, J = 15.6 Hz, 1H), 3.41 (d, J = 6.5 Hz, 1H), 1.94 (d, J = 12.7 Hz, 1H), 1.85-1.72 (m, 2H), 1.69 (d, J = 12.0 Hz, 2H), 1.67-1.58 (m, 1H), 1.35-1.13 (m, 4H), 1.12-1.02 (m, 1H) ppm

| 4 | (structure: cyclohexyl amino acetyl 4-fluoro-2-cyanopyrrolidine) | $C_{13}H_{21}FN_3O$ calc'd 254.1663 observed 254.1675 |
|---|---|---|

1H NMR (400 MHz, Methanol-d4): δ 5.30 (dt, J = 51.3, 3.3 Hz, 1H), 4.89 (d, J = 9.5 Hz, 1H), 3.96-3.54 (m, 3H), 2.52-2.18 (m, 2H), 1.80-1.46 (m, 6H), 1.26-0.96 (m, 5H) ppm

| 5 | (structure: propargyl-PEG-pyrrolidinyl cyclohexyl amino acetyl isoindoline) | $C_{25}H_{36}N_3O_3$ calc'd 426.2751 observed 426.2757 |
|---|---|---|

1H NMR (500 MHz, Methanol-d4) δ 7.41-7.33 (m, 4H), 5.06 (d, J = 13.9 Hz, 1H), 5.02-4.94 (m, 2H), 4.80 (d, J = 15.9 Hz, 1H), 4.33 (d, J = 29.2 Hz, 1H), 4.24 (d, J = 6.3 Hz, 1H), 4.21 (d, J = 2.4 Hz, 2H), 3.80-3.62 (m, 6H), 3.24-3.10 (m, 2H), 2.91 (s, 1H), 2.30 (s, 3H), 2.19 (d, J = 7.0 Hz, 1H), 2.11-1.95 (m, 3H), 1.48 (ddt, J = 61.9, 24.6, 10.9 Hz, 4H), 1.31 (s, 1H) ppm

| 6 | (structure: propargyloxy-pyrrolidinyl cyclohexyl amino acetyl isoindoline) | $C_{23}H_{32}N_3O_2$ calc'd 382.2489 observed 382.2495 |
|---|---|---|

1H NMR (500 MHz, Methanol-d4) δ 7.41-7.35 (m, 4H), 5.06 (d, J = 13.8 Hz, 1H), 4.98 (d, J = 14.1 Hz, 1H), 4.95 (s, 1H), 4.80 (d, J = 15.9 Hz, 1H), 4.52 (d, J = 30.4 Hz, 1H), 4.26 (d, J = 2.4 Hz, 2H), 4.23 (d, J = 6.3 Hz, 1H), 3.86-3.64 (m, 2H), 3.28-3.11 (m, 2H), 2.97 (t, J = 2.4 Hz, 1H), 2.32 (d, J = 24.1 Hz, 3H), 2.22 (d, J = 6.2 Hz, 1H), 2.11-1.96 (m, 4H), 1.64-1.51 (m, 2H), 1.51-1.36 (m, 2H) ppm Determination of Cell Kill (HIV-TACK) Activity:

Peripheral blood mononuclear cells (PBMCs) derived from healthy donors were stimulated in complete RPMI media (RPMI 1640 with L-glutamine; 10% Fetal Bovine Serum; 100 U/mL Penicillin-Streptomycin) containing 5 μg/mL Phytohemagglutinin (PHA) at about $1 \times 10^6$ cells/mL for 72 hours under the following conditions: 5% $CO_2$, 37° C., and 90% humidity. After 72 hours, the viability and cell count of PHA-stimulated PBMCs were determined using the Vi-CELL XR system (Beckman Coulter). PHA-stimulated PBMCs that measured >92% viability were qualified to move forward with viral infection. PHA-stimulated PBMCs were then centrifuged at 200×g for 5 minutes, and supernatant removed via aspiration for discard. PBMCs were resuspended at about $1 \times 10^7$ cells/mL in complete RPMI media with IL-2 (10 U/mL) and infected with VSV-G pseudotyped HIV virus stock (VSV-G/pNLG1-P2A-AEnv) to achieve <5% infectivity. PBMCs were then incubated for 4 hours at 37° C., 5% $CO_2$ and 90% humidity. Infected PBMCs were washed by centrifuging at 200×g for 5 minutes at 22° C. three times with complete RPMI media plus 10 U/mL IL-2, and finally resuspended at about $5 \times 10^6$ cells/mL in the same media. The infected PBMCs were incubated for 24 hours under the standard conditions (37° C., 5% $CO_2$ and 90% humidity) prior to compound/control treatments.

Compounds and controls were solvated in dimethyl sulfoxide (DMSO) and transferred using focused acoustic energy by an Echo 555 liquid handling instrument into designated wells of uniquely bar coded 384 Poly-D-Lysine coated, clear-bottomed assay plates. Compound dose response curves were prepared in a 10-point, 3-fold fashion within columns 3-12 with the pattern repeated in columns 13-22 from high to low compound concentrations. No compounds were dispensed in the outer edge wells of the assay plate. The final assay concentration of typical dose response curves ranged from 40.5 μM to 2.05 nM (0.5% DMSO final assay concentration). Controls included no inhibitor (DMSO only) and the maximal effect control Staurosporine at a final assay concentration of 4 μM. To test the effects of indinavir (protease inhibitor) on TACK activity, a final assay concentration of 300 nM indinavir was pre-plated onto the assay plates.

For compound treatment, at 24 hours post infection, the PBMCs were counted for total number of cells and measured for cell viability using the Vi-CELL XR. Infected PBMCs were centrifuged at 200×g for 5 minutes at 22° C., supernatant removed by aspiration, then the cells were diluted to a final concentration of $4 \times 10^5$ cells/mL in complete RPMI media plus IL-2 (10 U/mL). Infected PBMCs (20,000 cells, 50 μL/well) were transferred with a Bravo SRT liquid hander using disposable tips onto the assay plates. The lidded assay plates were incubated for 72 hours under the standard conditions (37° C., 5% CO2 and 90% humidity). Following the incubation period, plates were scanned on an Acumen ex3 imager (488 nm laser) and the number of GFP positive objects per well were recorded. Loss of GFP represented death of infected cells. Dose response curves and $EC_{50}$ values were calculated using a four-parameter logistic fit. Results are shown in Table 2.

TABLE 2

| Ex. No. | TACK $EC_{50}$ (nM) |
|---|---|
| 1 | 211 |
| 2 | 6423 |
| 3 | 1410 |

TABLE 2-continued

| Ex. No. | TACK $EC_{50}$ (nM) |
|---|---|
| 4 | 314 |
| 5 | 533 |
| 6 | 230 |

What is claimed is:
1. A compound that is

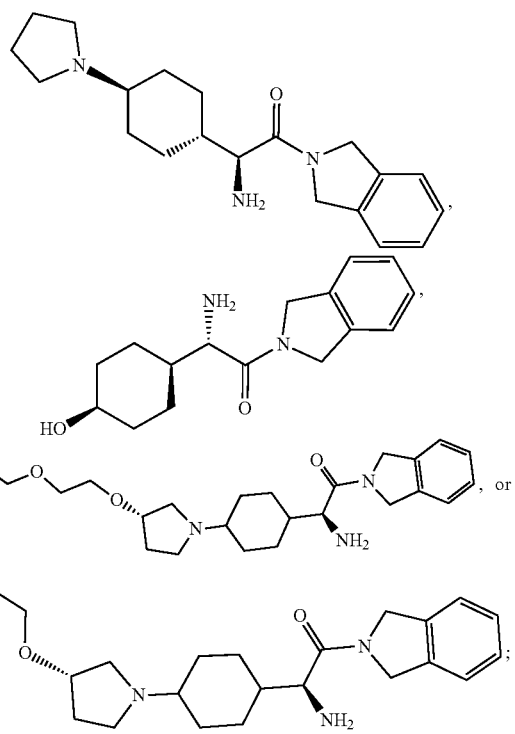

or a pharmaceutically acceptable salt thereof.

2. The compound of claim 1, or a pharmaceutically acceptable salt thereof, for use in a method for treatment or prophylaxis of infection by HIV, or for the treatment, prophylaxis or delay in the onset or progression of AIDS or ARC in a human subject.

3. A pharmaceutical composition comprising an effective amount of the compound according to claim 1, or a pharmaceutically acceptable salt thereof, and a pharmaceutically acceptable carrier.

4. The pharmaceutical composition of claim 3 further comprising an effective amount of one or more additional nucleoside or nucleotide HIV reverse transcriptase inhibitors, nucleoside or nucleotide reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

5. A method for the treatment or prophylaxis of infection by HIV, or for the treatment, prophylaxis or delay in the onset or progression of AIDS or ARC in a human subject in need thereof which comprises administering to the subject an effective amount of the compound according to claim 1, or a pharmaceutically acceptable salt thereof.

6. The method of claim 5 further comprising administering to the human subject an effective amount of one or more additional compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

7. A method for eliciting GAG-POL dimerization in HIV-infected cells in a human subject in need thereof which comprises administering to the subject an effective amount of the compound according to claim 1, or a pharmaceutically acceptable salt thereof.

8. A method for selectively killing HIV infected GAG-POL expressing cells in a human subject which comprises administering to the subject an effective amount of the compound according to claim 1, or a pharmaceutically acceptable salt thereof.

9. A method for selectively killing HIV infected GAG-POL expressing cells without concomitant cytotoxicity to HIV naïve cells in a human subject which comprises administering to the human subject an effective amount of the compound according to claim 1, or a pharmaceutically acceptable salt thereof.

10. A method for augmenting the suppression of HIV viremia in a human subject whose viremia is being suppressed by administration of one or more compatible HIV antiviral agents, which comprises additionally administering to the subject an effective amount of the compound according to claim 1, or a pharmaceutically acceptable salt thereof.

* * * * *